(12) United States Patent
Cesco-Cancian

(10) Patent No.: US 6,168,585 B1
(45) Date of Patent: *Jan. 2, 2001

(54) DISPOSABLE TRAINING PANT WITH ELASTICALLY SUSPENDED ABSORBENT ASSEMBLY

(75) Inventor: Annamaria Cesco-Cancian, Kimberly, WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/167,692

(22) Filed: Dec. 15, 1993

(51) Int. Cl.⁷ ........................................ A61F 13/15
(52) U.S. Cl. ........................... 604/385.2; 604/358
(58) Field of Search ................. 604/358, 367–369, 604/373, 385.1, 385.2, 386, 392, 393, 394, 396, 397, 398, 400

(56) References Cited

U.S. PATENT DOCUMENTS

| | | |
|---|---|---|
| Re. 30,029 | 6/1979 | Smith . |
| 1,931,357 | 10/1933 | Potwin . |
| 2,102,359 | 12/1937 | Frieman . |
| 2,122,417 | 7/1938 | Fridolph . |
| 2,166,012 | 7/1939 | La Maida . |
| 2,252,019 | 8/1941 | Meinecke et al. . |
| 2,252,992 | 8/1941 | Steiner . |
| 2,397,641 | 4/1946 | Blair . |
| 2,435,945 | 2/1948 | Redmond . |
| 2,450,059 | 9/1948 | Rickerson . |
| 2,450,789 | 10/1948 | Frieman . |
| 2,530,647 | 11/1950 | Buchler . |
| 2,538,596 | 1/1951 | Sheridan . |
| 2,551,663 * | 5/1951 | Fox ...................................... 604/369 |
| 2,639,239 | 5/1953 | Elliott . |

(List continued on next page.)

FOREIGN PATENT DOCUMENTS

| | | |
|---|---|---|
| 72696/91 | 9/1991 | (AU) . |
| 3343622A1 | 6/1985 | (DE) . |
| 0187728 | 7/1986 | (EP) . |
| 0456885A1 | 11/1991 | (EP) . |
| 0487921A2 | 3/1992 | (EP) . |
| 0539703A1 | 5/1993 | (EP) . |
| 0549988 | 7/1993 | (EP) . |
| 0567792 | 11/1993 | (EP) . |
| 615737A2 | 3/1994 | (EP) . |
| 619953A1 | 4/1994 | (EP) . |
| 627177A1 | 5/1994 | (EP) . |
| 627178A1 | 5/1994 | (EP) . |
| 0661031A2 | 7/1995 | (EP) . |
| 0679754 | 9/1952 | (GB) . |
| 0774712 | 5/1957 | (GB) . |

(List continued on next page.)

Primary Examiner—John G. Weiss
Assistant Examiner—Dennis Ruhl
(74) Attorney, Agent, or Firm—Thomas M. Gage (57) ABSTRACT

An absorbent garment includes an outer cover defining opposite waist regions and an elastically suspended absorbent assembly. The absorbent assembly, which has a longitudinal axis and opposite longitudinally spaced ends, includes an absorbent core and a moisture barrier. The garment also includes a tummy band formed of an elastic material and operatively joined to the outer cover adjacent at least a portion of one of the waist regions. In one embodiment, the tummy band is capable of stretching in first and second substantially perpendicular directions and elastically connects one end of the absorbent assembly and the outer cover. In an alternate embodiment, the tummy band elasticizes a portion of one waist region and a suspension member elastically connects one end of the absorbent assembly and the outer cover.

19 Claims, 8 Drawing Sheets

U.S. PATENT DOCUMENTS

| | | |
|---|---|---|
| 2,688,328 | 9/1954 | Marcus . |
| 2,733,715 | 2/1956 | Folk . |
| 3,049,124 | 8/1962 | Thompson . |
| 3,087,495 | 4/1963 | Hart . |
| 3,098,484 | 7/1963 | Younger . |
| 3,142,301 | 7/1964 | Erteszek . |
| 3,162,196 | 12/1964 | Salk . |
| 3,192,926 | 7/1965 | Callaghan . |
| 3,211,147 | 10/1965 | Pherson et al. . |
| 3,237,625 | 3/1966 | Johnson . |
| 3,368,563 | 2/1968 | Scheier . |
| 3,386,446 | 6/1968 | Sloan . |
| 3,397,696 | 8/1968 | Rickard . |
| 3,420,236 * | 1/1969 | De Woskin ............................ 604/398 |
| 3,424,162 | 1/1969 | Parravicini . |
| 3,589,364 | 6/1971 | Dean et al. . |
| 3,595,235 | 7/1971 | Jespersen . |
| 3,599,640 | 8/1971 | Larson . |
| 3,613,687 | 10/1971 | Kennedy . |
| 3,635,221 | 1/1972 | Champaigne, Jr. . |
| 3,687,141 | 8/1972 | Matsuda . |
| 3,768,481 | 10/1973 | Shibata . |
| 4,019,517 | 4/1977 | Glassman . |
| 4,022,210 | 5/1977 | Glassman . |
| 4,025,472 | 5/1977 | Lepoutre . |
| 4,031,568 | 6/1977 | Huff . |
| 4,041,121 | 8/1977 | Smith . |
| 4,067,068 | 1/1978 | Bregstein et al. . |
| 4,072,150 | 2/1978 | Glassman . |
| 4,122,552 | 10/1978 | Tedford . |
| 4,205,679 | 6/1980 | Repke et al. . |
| 4,227,531 | 10/1980 | McLeod . |
| 4,256,111 | 3/1981 | Lassen . |
| 4,265,245 | 5/1981 | Glassman . |
| 4,285,342 | 8/1981 | Mesek . |
| 4,340,563 | 7/1982 | Appel et al. . |
| 4,351,340 | 9/1982 | McLeod . |
| 4,352,356 | 10/1982 | Tong . |
| 4,355,425 | 10/1982 | Jones et al. . |
| 4,388,075 | 6/1983 | Mesek et al. . |
| 4,405,297 | 9/1983 | Appel et al. . |
| 4,407,284 | 10/1983 | Pieniak . |
| 4,425,128 | 1/1984 | Motomura . |
| 4,427,408 | 1/1984 | Karami et al. . |
| 4,430,086 | 2/1984 | Repke . |
| 4,486,192 * | 12/1984 | Sigl ....................................... 604/370 |
| 4,496,360 | 1/1985 | Joffe et al. . |
| 4,555,245 | 11/1985 | Armbruster . |
| 4,578,073 | 3/1986 | Dysart et al. . |
| 4,597,760 | 7/1986 | Buell . |
| 4,597,761 | 7/1986 | Buell . |
| 4,606,964 | 8/1986 | Wideman . |
| 4,610,678 * | 9/1986 | Weisman et al. ..................... 604/368 |
| 4,610,680 | 9/1986 | LaFleur . |
| 4,610,681 | 9/1986 | Strohbeen et al. . |
| 4,619,649 | 10/1986 | Roberts . |
| 4,630,320 | 12/1986 | Van Gompel . |
| 4,639,949 * | 2/1987 | Ales et al. . |
| 4,641,381 * | 2/1987 | Heran et al. . |
| 4,642,819 * | 2/1987 | Ales et al. . |
| 4,643,728 * | 2/1987 | Karami ................................ 604/370 |
| 4,646,362 * | 3/1987 | Heran et al. . |
| 4,655,760 * | 4/1987 | Morman et al. . |
| 4,657,802 * | 4/1987 | Morman . |
| 4,662,877 | 5/1987 | Williams . |
| 4,671,793 | 6/1987 | Hults et al. . |
| 4,677,695 * | 7/1987 | Van Gompel et al. . |
| 4,690,681 * | 9/1987 | Haunschild et al. . |
| 4,692,368 | 9/1987 | Taylor et al. . |
| 4,695,279 * | 9/1987 | Steer . |
| 4,704,116 | 11/1987 | Enloe . |
| 4,710,187 | 12/1987 | Boland et al. . |
| 4,718,902 | 1/1988 | Bonito . |
| 4,720,415 * | 1/1988 | Vander Wielen et al. . |
| 4,735,622 * | 4/1988 | Acuff et al. . |
| 4,743,239 * | 5/1988 | Cole . |
| 4,743,241 * | 5/1988 | Igaue et al. . |
| 4,747,846 | 5/1988 | Boland et al. . |
| 4,753,648 * | 6/1988 | Jackson ............................... 604/393 |
| 4,756,709 | 7/1988 | Stevens . |
| 4,771,483 * | 9/1988 | Hooreman et al. . |
| 4,798,603 | 1/1989 | Meyer et al. . |
| 4,808,176 | 2/1989 | Kielpikowski . |
| 4,834,736 | 5/1989 | Boland et al. . |
| 4,834,737 | 5/1989 | Khan . |
| 4,846,823 | 7/1989 | Enloe . |
| 4,846,825 | 7/1989 | Enloe et al. . |
| 4,892,536 | 1/1990 | DesMarais et al. . |
| 4,892,598 | 1/1990 | Stevens et al. . |
| 4,909,804 * | 3/1990 | Douglas, Sr. . |
| 4,935,021 | 6/1990 | Huffman et al. . |
| 4,938,753 * | 7/1990 | Van Gompel et al. . |
| 4,938,754 * | 7/1990 | Mesek . |
| 4,938,757 * | 7/1990 | Van Gompel et al. . |
| 4,940,464 * | 7/1990 | Van Gompel et al. . |
| 4,955,880 * | 9/1990 | Rodriquez . |
| 4,961,234 | 10/1990 | Leibman . |
| 4,964,857 * | 10/1990 | Osborn . |
| 4,968,312 * | 11/1990 | Khan . |
| 5,019,068 * | 5/1991 | Perez et al. . |
| 5,055,103 * | 10/1991 | Nomura et al. . |
| 5,062,839 * | 11/1991 | Anderson . |
| 5,074,854 * | 12/1991 | Davis . |
| 5,080,741 * | 1/1992 | Nomura et al. . |
| 5,087,253 * | 2/1992 | Cooper . |
| 5,092,861 * | 3/1992 | Nomura et al. . |
| 5,108,385 * | 4/1992 | Snyder . |
| 5,114,781 * | 5/1992 | Morman . |
| 5,116,662 * | 5/1992 | Morman . |
| 5,163,932 * | 11/1992 | Nomura et al. . |
| 5,171,239 * | 12/1992 | Igaue et al. . |
| 5,176,672 * | 1/1993 | Bruemmer et al. . |
| 5,188,627 * | 2/1993 | Igaue et al. . |
| 5,197,960 * | 3/1993 | Nomura et al. . |
| 5,204,997 * | 4/1993 | Suzuki et al. . |
| 5,236,430 * | 8/1993 | Bridges . |
| 5,246,433 * | 9/1993 | Hasse et al. . |
| 5,389,095 | 2/1995 | Suzuki et al. . |
| 5,435,014 | 7/1995 | Moretz et al. . |
| 5,499,978 | 3/1996 | Buell et al. . |
| 5,507,736 | 4/1996 | Clear et al. . |

FOREIGN PATENT DOCUMENTS

| | | |
|---|---|---|
| 0779461 | 7/1957 | (GB) . |
| 0849573 | 9/1960 | (GB) . |
| 1520740 | 8/1978 | (GB) . |
| 2103930 | 3/1983 | (GB) . |
| 2242610 | 10/1991 | (GB) . |
| 2244201 | 11/1991 | (GB) . |
| 2244422 | 12/1991 | (GB) . |
| 2244909 | 12/1991 | (GB) . |
| 2253131 | 9/1992 | (GB) . |
| 2254997 | 10/1992 | (GB) . |
| 2256803 | 12/1992 | (GB) . |
| 2257347 | 1/1993 | (GB) . |
| 2259441 | 3/1993 | (GB) . |
| 2268073 | 1/1994 | (GB) . |
| 2268389 | 1/1994 | (GB) . |
| 2275611 | 9/1994 | (GB) . |
| WO 89/11842 | 12/1989 | (WO) . |
| WO 91/10413 | 7/1991 | (WO) . |

WO 91/16871    11/1991  (WO).
WO 92/00051     1/1992  (WO).
WO 93/09742     5/1993  (WO).
WO 93/09746     5/1993  (WO).
WO 93/17648  *  9/1993  (WO).

WO 94/14394     7/1994  (WO).
WO 95/16418     6/1995  (WO).
WO 95/16419     6/1995  (WO).

* cited by examiner

DISPOSABLE TRAINING PANT WITH ELASTICALLY SUSPENDED ABSORBENT ASSEMBLY

BACKGROUND OF THE INVENTION

The present invention relates generally to disposable absorbent garments. More particularly, the invention pertains to a child's disposable training pant having a full outer cover and an elastically suspended absorbent assembly. The invention also pertains to a method of making a three-dimensional absorbent garment.

The use of disposable absorbent training pants during the period when a child is toilet training has become increasingly popular. The parent or parents will generally undertake toilet training when the child reaches an age in the range of about 15 to 30 months. The aim is for the child to become independent of the parent or caretaker in using the toilet.

Training pants represent an intermediate stage for a child between having diapers applied and using underpants by himself or herself. As such, it is important for training pants to be three-dimensional articles like underpants, rather than two-dimensional articles like disposable diapers. A suitable disposable training pant, therefore, is an article having closed sides and defining waist and leg openings. Hopefully, the child will raise and lower the pant whenever necessary without requiring the aid of a parent. To wear the training pant, the child places his or her feet in the waist and respective leg openings and pulls the pant upwardly along the legs to raise the pant to the crotch. This is significantly different from the way a two-dimensional diaper is secured to child.

Despite the child's best efforts, though, it is highly probable that the child will, on occasion, void while wearing the training pant. Accordingly, the training pant must absorb and contain body waste. Training pants have heretofore been formed primarily as composite structures of which an absorbent core is merely a component. Unfortunately, forces affecting the position of the outer cover in such composite structures also tend to affect the position of the absorbent core. This can impact absorbency and containment characteristics, particularly when considering the typical activity level of a child at the age of toilet training.

SUMMARY OF THE INVENTION

Thus, there is a need to provide an improved child's training pant that minimizes the transferral of exterior forces from the outer cover to the absorbent core. In response to this need, a new absorbent garment and method of making an absorbent garment have been discovered. An absorbent garment according to the invention includes an outer cover defining opposite waist regions, and an absorbent assembly having a longitudinal axis and opposite longitudinally spaced ends. The absorbent assembly comprises an absorbent core and a moisture barrier. A tummy band of the garment is formed of an elastic material capable of stretching in first and second substantially perpendicular directions and is operatively joined to the outer cover adjacent at least a portion of one of the waist regions. The tummy band elastically connects one end of the absorbent assembly and the outer cover, in a manner such that the first direction is generally parallel to the longitudinal axis of the absorbent assembly.

This aspect of the invention provides an absorbent garment that minimizes transference of forces from the outer cover to the absorbent assembly. The tummy band, being stretchable in at least two directions, allows the outer cover to move substantially independently of the absorbent assembly. As a result, the absorbent structure can remain snugly in place and resist movement in response to movements of the outer cover. This is particularly significant with relatively thin absorbent assemblies which tend to be readily influenced by movements of the outer cover. In particular embodiments of the invention, the absorbent core has a bulk thickness of not more than about 0.6 centimeter.

In another aspect of the invention, a three-dimensional absorbent garment includes a full outer cover. The full outer cover has opposite inner and outer surfaces and defines a waist opening and a pair of leg openings. A tummy band formed of an elastic material is operatively joined to the outer cover adjacent at least a portion of the waist opening. An absorbent assembly of the garment has a longitudinal axis, opposite longitudinally spaced ends, and side edges extending between the ends. The absorbent assembly includes a liquid permeable liner, a liquid impermeable moisture barrier attached to the liner, and an absorbent core sandwiched between the liner and moisture barrier. One or more suspension members, each formed of an elastic material, elastically connect the ends of the absorbent assembly and the inner surface of the outer cover. Each suspension member is extendable in a direction generally parallel to the longitudinal axis of the absorbent assembly. This aspect provides the same benefits described above, but does not require the use of an elastic material that can stretch in two substantially perpendicular directions.

Another aspect of the invention relates to a method of making a three-dimensional absorbent garment. The method includes: supplying an outer cover having opposite longitudinally spaced waist regions and opposite side panels extending between the waist regions; elasticizing at least a portion of one waist region; supplying an absorbent assembly having a longitudinal axis and opposite longitudinally spaced ends, the absorbent assembly comprising an absorbent core and a moisture barrier; elastically connecting one end of the absorbent assembly and a waist region of the outer cover, the elastic connection being extendable in a direction generally parallel to the longitudinal axis of the absorbent assembly; and bonding portions of each side panel together to define a waist opening and a pair of leg openings.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed", "disposed on", "disposed with", "disposed at", "disposed near", and variations thereof are intended to mean that one element can be integral with another element, or that one element can be a separate structure joined to or connected to or placed with or placed near another element.

(d) "elastic" and "elasticity" include that property of a material by virtue of which it tends to recover its original size and shape after removal of a force causing the deformation.

(e) "elastically connected" and "elastically connecting" refer to two elements being separated by and bonded to an elastic member, where the relative position of the two elements may change due to extension of the elastic member.

(f) "elongation" includes the ratio of the extension of a material to the length of a material prior to stretching, expressed in percent.

(g) "extension", "extend", and "extended" include the change in length of a material due to stretching, expressed in units of length.

(h) "force" includes a physical influence exerted by one body on another which produces acceleration of bodies that are free to move and deformation of bodies that are not free to move. Force is expressed in grams per unit area.

(i) "foreshortened" and "foreshortening" include to shorten beforehand, that is, before a subsequent step.

(j) "front" and "back" are used to designate relationships relative to the garment itself, rather than to suggest any position the garment assumes when it is positioned on a wearer.

(k) "member" when used in the singular can have the dual meaning of a single element or a plurality of elements.

(l) "operatively joined", with reference to the attachment of an elastic member to another element, means that the elastic member when attached to or connected to the element, or treated with heat, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(m) "rupture" includes the breaking or tearing apart of a material; in tensile testing, rupture refers to the total separation of a material into two parts either all at once or in stages, or the development of a hole in some materials.

(n) "stretch bonded" refers to an elastomeric strand being bonded to another member while the elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(o) "stretch bonded laminate" refers to a composite material having at least two layers in which one layer is a gatherable layer and the other layer is a stretchable, that is, elastic, layer. The layers are joined together when the stretchable layer is in a stretched condition so that upon relaxing the layers, the gatherable layer is gathered.

(p) "tension" includes a uniaxial force tending to cause the extension of a body or the balancing force within that body resisting the extension.

(q) "three dimensional" refers to a garment similar to underwear, shorts or pants in that it has continuous leg and waist openings that are bounded by material of which the garment is made. The garment may or may not have manually tearable seams.

(r) "two dimensional" refers to a garment that can be opened without destructively tearing any structure while being laid in a flat condition. These garments, such as diapers, do not have continuous leg and waist openings, and require a fastening device, such as adhesive tapes or hook-and-loop fasteners, to attach the garment about the wearer.

(s) "ultimate elongation" includes the elongation at the point of rupture.

These definitions are not intended to be limiting, and these terms may be defined with additional language in the remaining portion of the specification.

DETAILED DESCRIPTION OF THE PREFERRED EMBODIMENTS

Figure 1:
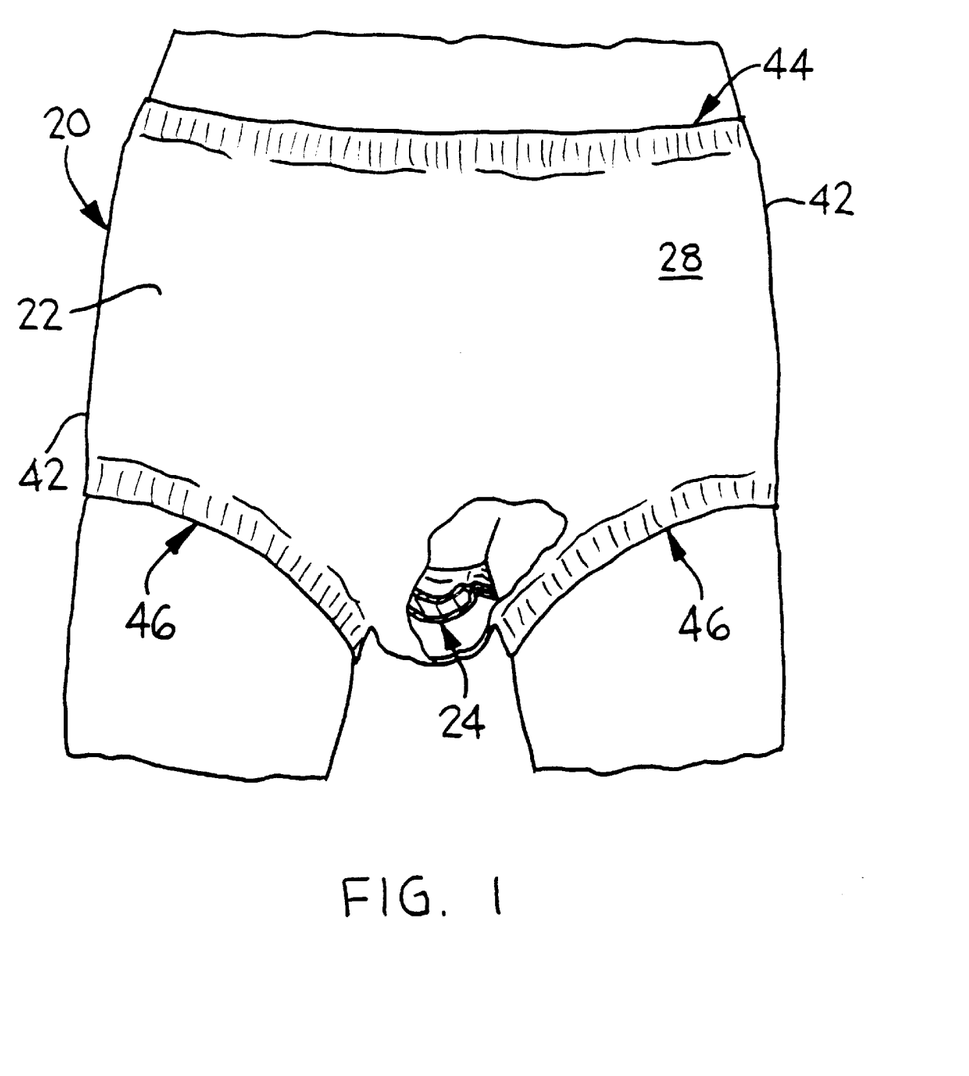
FIG. 1 is a front view of a three-dimensional absorbent garment according to the present invention shown on a wearer, with portions broken away for the purposes of illustration.
Figure 2:
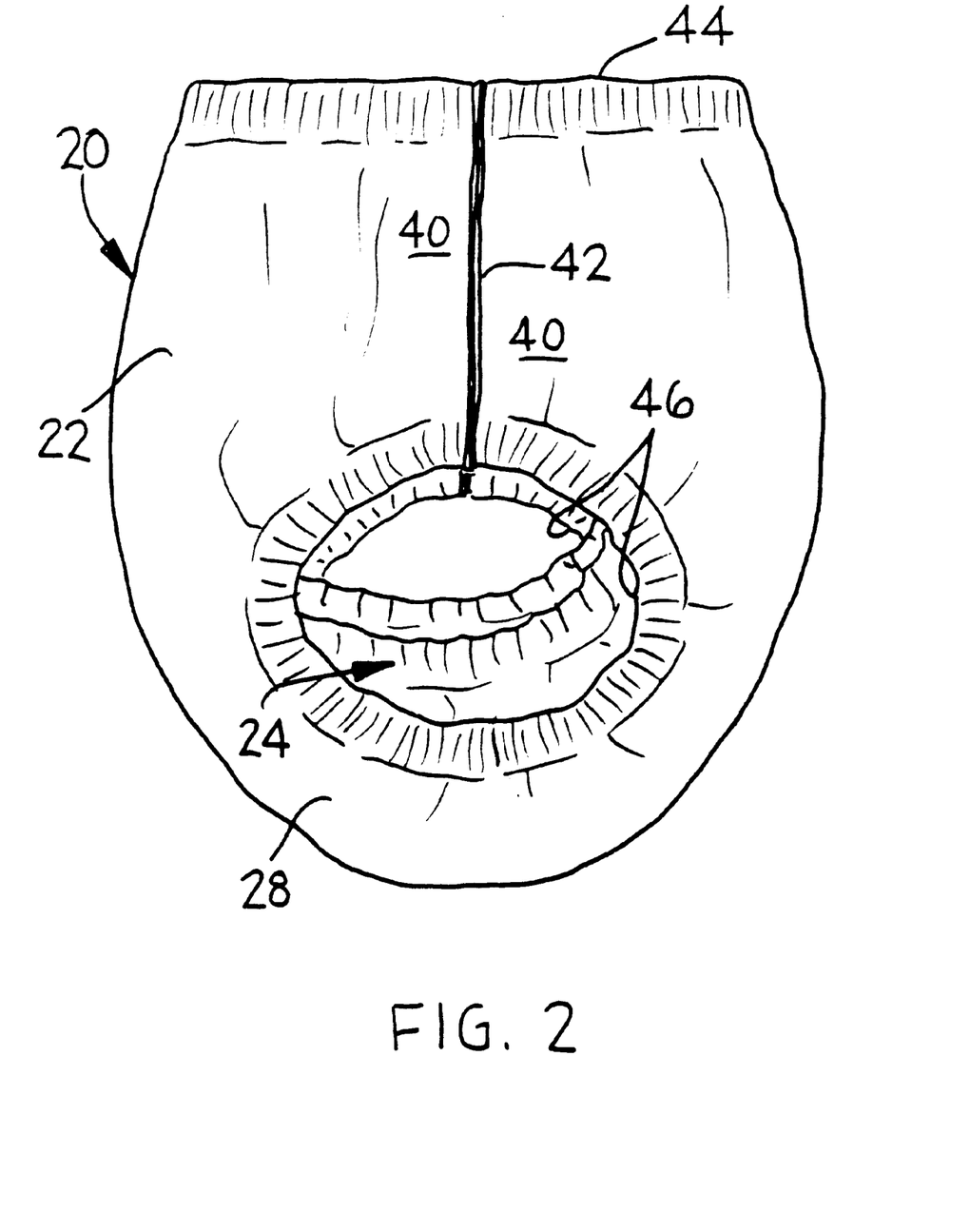
FIG. 2 is a side view of the absorbent garment shown in FIG. 1.

With reference to FIGS. 1 and 2, a disposable absorbent garment 20 formed according to the present invention is shown for purposes of illustration as a three-dimensional training pant for a child. The invention may also be embodied in other types of garments, such as adult incontinence products.

The training pant 20 is shown fitted, that is pulled fully upward to the waist, on a child's torso in FIG. 1, and shown by itself in side view in FIG. 2. The training pant 20 includes a full outer cover 22 and a suspended absorbent assembly 24. The training pant 20 is intended to resemble underwear, although it may be designed as clothing apparel (see FIG. 10). The present invention minimizes the transference of forces from the outer cover 22 to the absorbent assembly 24. At the same time, the training pant 20 is constructed such that the outer cover 22 remains securely in place about the child's waist with the absorbent assembly 24 positioned to receive and contain voided material.

Figure 3:
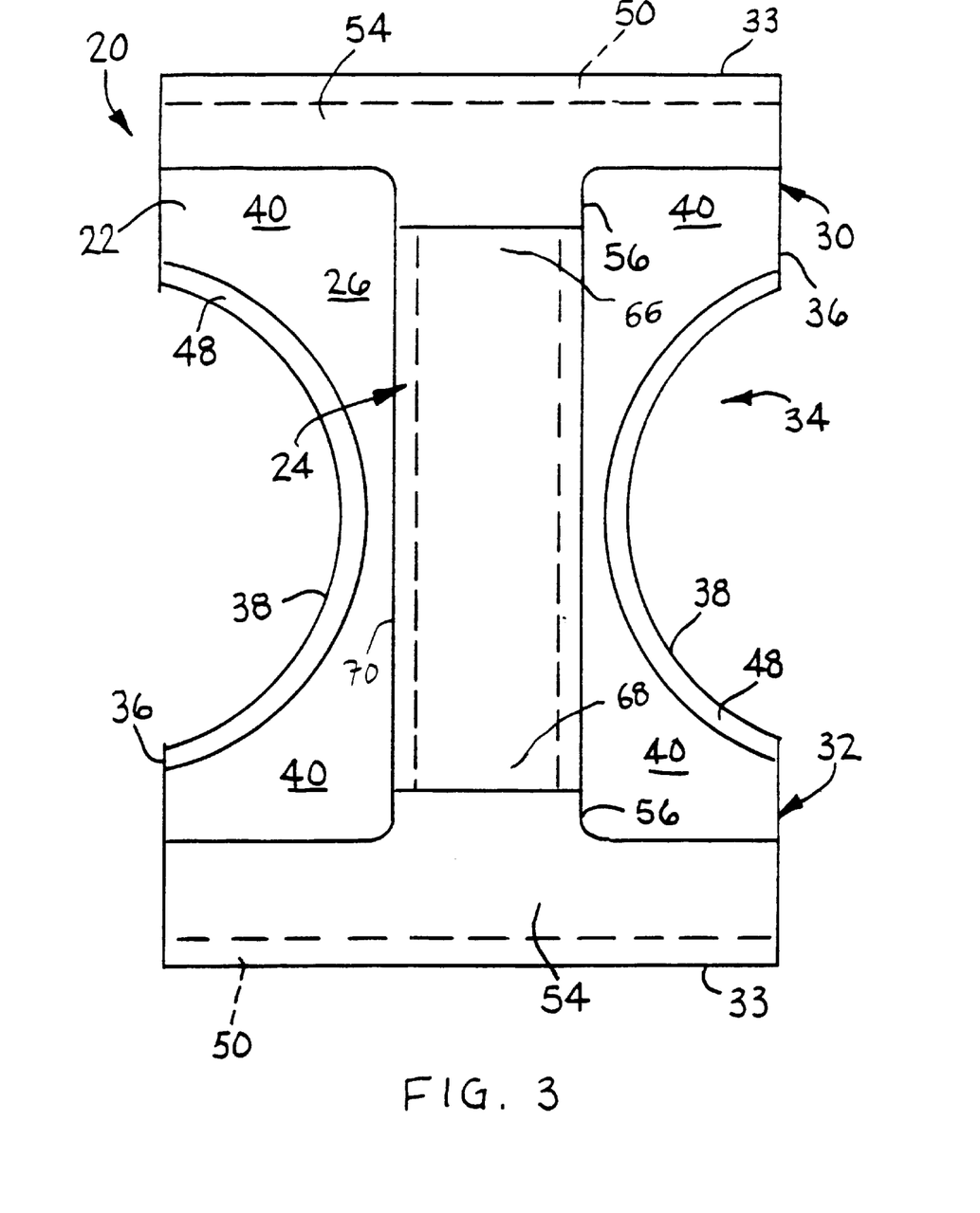
FIG. 3 is a plan view of the absorbent garment shown in FIG. 1, at an intermediate stage of assembly and in a stretched condition.

The training pant 20 is illustrated in an intermediate stage of assembly and in a stretched condition in FIG. 3. The outer cover 22 is referred to as a full outer cover because it generally provides the three dimensional shape of the garment 20. The outer cover 22 includes opposite inner and outer surfaces 26 and 28, of which only the inner surface 26 appears in FIG. 3. The outer cover 22 also includes front and back longitudinally spaced waist regions 30 and 32, which terminate in longitudinal ends 33 of the training pant 20. A crotch area 34 is located between the front and back waist regions 30 and 32. Opposite side panels 36 extend between the front and back waist regions 30 and 32. Each side panel 36 is preferably shaped to form a recessed area 38 with ear portions 40 on either end of the recessed area.

As illustrated most clearly in FIG. 2, the ear portions 40 of each side panel 36 are bonded together in the finished pant by manually tearable, non-refastenable seams 42. The seams 42 may be formed by any suitable means such as ultrasonic sealing, adhesive bonding, heat sealing, adhesive coated tapes, or the like. One suitable method of forming such seams is disclosed in U.S. Pat. No. 4,938,753 issued Jul. 3, 1990, to Van Gompel et al., which is incorporated herein by reference. The outer cover 22 thus defines a waist opening 44 and a pair of leg openings 46 (FIGS. 1 and 2).

The underwear-like appearance of the training pant 20 is in part the result of elasticizing the waist and leg openings 44 and 46. In particular, leg elastic bands 48 (FIG. 3) are operatively joined to the outer cover 22 along the recessed area 38 of each side panel 36. Also, waist elastic bands 50 are operatively joined to the outer cover 22 along the longitudinal ends 33 of each waist region 30 and 32. The leg and waist elastic bands 48 and 50 may be bonded to the outer cover 22 using adhesives, thermal bonds, ultrasonic bonds, stitching, or other suitable means. The elastic bands 48 and 50 may be stretch bonded to the outer cover 22 or bonded in a relaxed state to a gathered portion of the outer cover. One suitable method for attaching the leg and waist elastic bands 48 and 50 is disclosed in U.S. Pat. No. 4,639,949 issued Feb. 7, 1987, to Ales et al., which is incorporated herein by reference.

The training pant 20 as illustrated includes a pair of tummy bands 54 formed of an elastic material capable of stretching in at least two directions. Desirably, the tummy bands 54 are capable of stretching in first and second substantially perpendicular directions. Each tummy band 54 is operatively joined to the outer cover 22 adjacent a longitudinal end 33 of the outer cover at a waist region 30 or 32. The first direction of stretchability of each tummy band 54 is preferably aligned with the longitudinal axis of the training pant 20, and correspondingly, the second direction of stretchability is aligned with the transverse axis of the training pant. The longitudinal and transverse axes of the training pant 20 lie in the plane of the garment, and in the illustrated embodiments the garment is longer in the longitudinal direction than in the transverse direction.

One function of the tummy band 54 is to secure the training pant 20 about the wearer's waist. Thus, the elastic tummy band material should possess sufficient elongation potential in the second direction to accommodate extension of the tummy bands when the training pant 20 is being fitted. Also, the tummy bands 54 should possess sufficient elasticity in the second direction to snugly yet not uncomfortably maintain the garment 20 in place. A suitable tummy band material should be capable of from about 10 to about 500 percent elongation and upon release of tension will recover at least 55 percent of its elongation. It is generally preferred that the tummy band material in the second direction be capable of between about 50 and about 300 percent elongation, particularly at least 125 percent elongation, and recovery upon release of tension of at least 80 percent of its elongation.

Each tummy band 54 desirably extends fully between the side panels 36 at each waist region 30 and 32. Alternately, the tummy bands 54 may be operatively joined to the outer cover 22 adjacent only a portion of the waist opening 44. Still alternately, only a single tummy band 54 may be operatively joined to one waist region 30 or 32 of the outer cover 22 adjacent the waist opening 44.

The tummy bands 54 may be positioned substantially coincident with the longitudinal ends 33 of the outer cover 22. Alternately, the tummy bands 54 could be spaced from the longitudinal ends 33, particularly spaced by from 0 to about 2.5 centimeters, particularly 0 to 2 centimeters. The tummy bands 54 have a width dimension extending parallel to the longitudinal axis of the training pant 20. This width dimension is generally a function of the total garment length, measured between the longitudinal ends 33 when in an unstretched condition. Suitably, the tummy bands 54 have a width dimension of from about 10 to about 50 percent, desirably from about 20 to about 40 percent, of the total garment length. For example, the tummy bands 54 may be between about 5 and 8 centimeters in width. Midway between the side panels 36, each tummy band 54 may include an extended portion 56 that is wider than other portions of the tummy band. The extended portion 56 serves primarily as an attachment area for the absorbent assembly 24.

Figure 4:
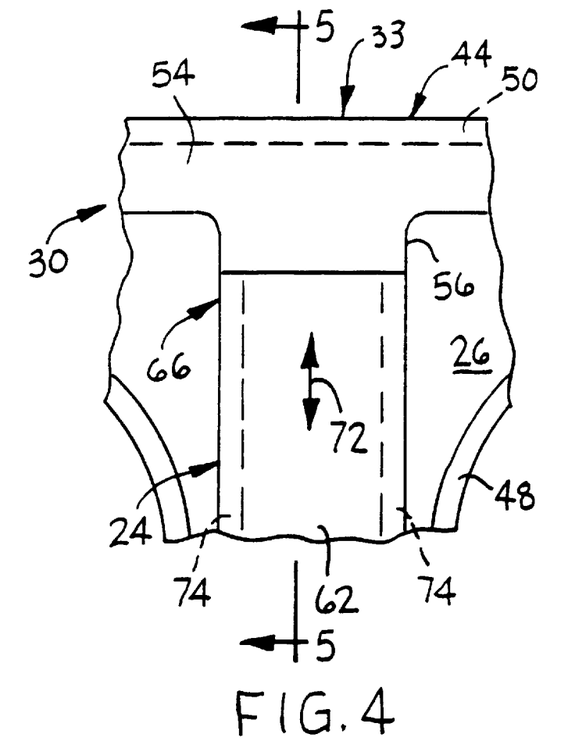
FIG. 4 is an enlarged view illustrating the connection of an absorbent assembly and an outer cover of the absorbent garment shown in FIG. 1.
Figure 5:
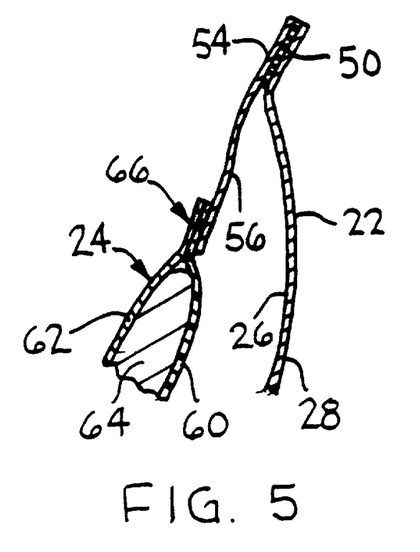
FIG. 5 is a view in section taken generally from the plane of the line 5—5 in FIG. 4.
Figure 6:
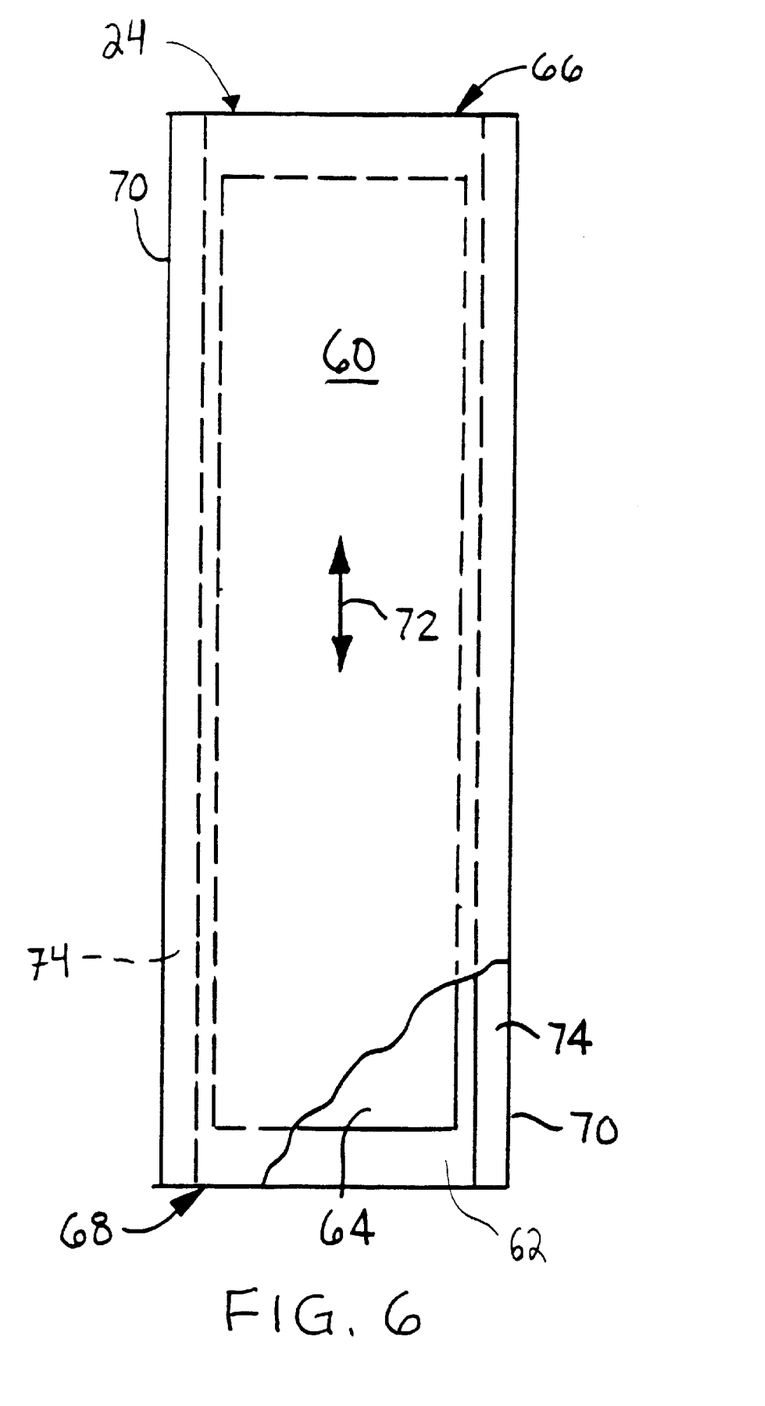
FIG. 6 is a bottom plan view of the absorbent assembly shown in FIGS. 1–5, with portions broken away for the purposes of illustration.

With additional reference to FIGS. 4–6, the absorbent assembly 24 as illustrated includes a substantially liquid impermeable moisture barrier 60, a substantially liquid permeable bodyside liner 62, and an absorbent core 64 sandwiched between the moisture barrier and the bodyside liner. The moisture barrier 60 and bodyside liner 62 are desirably longer and wider than the absorbent core 64, so that the peripheries of the moisture barrier and liner form margins which may be sealed together using ultrasonic bonds, thermal bonds, adhesives, or other suitable means. The absorbent core 64 may be attached to the moisture barrier 60 and/or the bodyside liner 62 using ultrasonic bonds, adhesives, or other suitable means. The absorbent assembly 24 may also include additional components to assist in the acquisition, distribution and storage of waste material. For example, the absorbent assembly 24 may include a transport layer, such as described in U.S. Pat. No. 4,798,603 issued Jan. 17, 1989, to Meyer et al., or a surge management layer, such as described in European Patent Application EP 0 539 703 A1, published May 5, 1993, which patent and application are incorporated herein by reference.

The absorbent core 64 is desirably relatively thin to provide an overall thinness dimension to the training pant 20. The absorbent core 64 desirably has a bulk thickness which is not more than about 0.6 centimeter, and particularly not more than about 0.5 centimeter. The bulk thickness is determined under a restraining pressure of 0.2 pounds per square inch (1.38 kPa). Further, the absorbent core 64 suitably has an absorbent capacity of at least about 300 grams, and desirably at least about 500 grams, of synthetic urine.

To achieve the desired thinness and capacity, the absorbent core 64 may comprise a matrix of substantially hydrophilic fibers having distributed therein particulate high-absorbency material, as described in detail hereinafter. The hydrophilic fibers and high-absorbency particles may be provided in a fiber-to-particulate ratio which is less than 70:30, for example between about 30:70 and about 70:30, desirably between about 40:60 and about 60:40, and particularly between about 45:55 and about 55:45.

The absorbent assembly 24 as shown is generally rectangular with a front end 66, and opposite back end 68, and longitudinal sides 70 extending between the front and back ends. The absorbent assembly 24 defines a longitudinal axis, represented by arrow 72 in FIG. 4. By way of example, the absorbent assembly 24 in a garment 20 suitable for a child of about 7 to 11 kilograms may be rectangular with a length in the range of about 28 to about 40 centimeters and a width in the range of about 7.5 to about 14 centimeters. Of course, the absorbent assembly 24 may optionally be T-shaped, I-shaped, hourglass-shaped, or irregularly-shaped.

The absorbent assembly 24 also desirably includes cuff elastic bands 74 operatively joined to the moisture barrier 60, the bodyside liner 62, or both. The cuff elastic bands 74 are positioned along the side edges 70 and longitudinally oriented along each side margin of the absorbent assembly 24. The cuff elastic bands 74 may assist in holding the absorbent assembly 24 against the body of the wearer or forming seals or gaskets about the leg of the wearer. The leg elastic bands 48, in contrast, are not connected to the absorbent assembly 24 and function to draw the outer cover 22 against the wearer.

As shown most clearly in FIG. 5, the absorbent assembly 24 is elastically suspended independent of the outer cover 22. The term "independent" in this context means that while the absorbent assembly 24 is connected to the outer cover 22, the outer cover can move relative to the absorbent assembly. In particular, the tummy bands 54 elastically connect each end 66 and 68 of the absorbent assembly 24 and the outer cover 22. The tummy bands 54, specifically the extended portions 56, may be bonded to the moisture barrier 60, the bodyside liner 62, or both using adhesives, ultrasonic bonds, thermal bonds or other suitable means. Desirably, the absorbent assembly 24 is attached to the outer cover 22 indirectly only at the longitudinally spaced ends 66 and 68, and the central portion of the absorbent assembly between the ends is itself neither directly nor indirectly attached to the outer cover. Each end 66 and 68 of the absorbent assembly 24 as viewed in this context comprises from about 2 to about 9 percent, particularly from about 4 to about 6 percent, of the longitudinal length of the absorbent assembly, with the central portion representing the balance of the absorbent assembly length. Alternately, the absorbent assembly 24 may be elastically connected to the outer cover 22 only at one end 66 or 68 (not shown).

The absorbent assembly 24 is bonded to the tummy bands 54 so that the first direction of stretch of the tummy band material is generally parallel to the longitudinal axis 72 of the absorbent assembly (see FIG. 4). In this way, the absorbent assembly 24 is maintained against the wearer to receive exudate over a range of locations at which the training pant 20 may be fitted to the wearer. The elastic tummy band material desirably has stretch characteristic in the first direction such that it is capable of from about 10 to about 500 percent elongation and upon release of tension will recover at least 55 percent of its elongation. It is generally preferred that the tummy band material in the first direction be capable of between about 50 and about 300 percent elongation, particularly at least 125 percent elongation and recovery upon release of tension of at least 80 percent of its elongation.

The training pant 20 can be formed in a continuous process by supplying an outer cover material including individual portions that define a single outer cover having opposite longitudinally spaced waist regions 30 and 32 and opposite side panels 36 extending between the waist regions. The side panels 36 can be shaped by die cutters, water jet cutters or other suitable means to define the recessed areas 38 and ear portions 40. Leg and waist elastic bands 48 and 50 can be stretch bonded to the outer cover material along the recessed areas 38 and longitudinal ends 33, respectively.

Simultaneously, the absorbent assembly 24 can be constructed by supplying bodyside liner and moisture barrier materials and sandwiching an individual absorbent core 64 between the moisture barrier 60 and bodyside liner 62. The peripheries of the moisture barrier 60 and bodyside liner 62 outward of the absorbent core 64 can be sealed together with cuff elastic bands 64 stretch bonded therebetween along the side edges 70. Individual absorbent assembly 24 can then be cut from the continuous supply of moisture barrier and bodyside liner materials.

After supplying the elastic tummy band material 54, the absorbent assembly 24 can be elastically connected to the waist regions 30 and 32. The tummy bands 54 can be bonded to the ends 66 and 68 of the absorbent assembly 24 and also stretched bonded to the outer cover 22 transversely across the waist regions 30 and 32. Both the waist elastic bands 50 and the tummy bands 54 have the effect of elasticizing the waist regions 30 and 32 of the outer cover 22. Thereafter, the ear portions 40 of each side panel 36 can be bonded together by seams 42 so that the outer cover 22 defines the waist opening 44 and the pair of leg openings 46.

In use, the three-dimensional training pant 20 is fitted by inserting the wearer's feet through the waist opening 44 and respective leg openings 46. The pant 20 is then grasped near the waist opening 44 and pulled upwardly along the legs until the absorbent assembly 24 is snugly fit against the crotch of the wearer. The pant 20 will be held in place in part due to the waist elastic bands 50 but principally due to the tummy bands 54. The waist elastic bands 50 may be selected to give the pant 20 an underwear-like appearance (FIG. 1) and need not be relied upon to maintain the pant about the wearer.

The present invention minimizes transference of forces from the outer cover 22 to the absorbent assembly 24. Because the absorbent assembly 24 is elastically connected to the outer cover 22 at its ends 66 and 68 and not bonded to the outer cover in the central region, the outer cover can move substantially independently of the absorbent assembly. The elastically mounted absorbent structure 24 tends to remain snugly in place and resist movement in response to movements of the outer cover 22. This is particularly significant where relatively thin absorbent assemblies are employed, because thin, light weight absorbent assemblies tend to track more drastically to movements of the outer cover.

Figure 7:
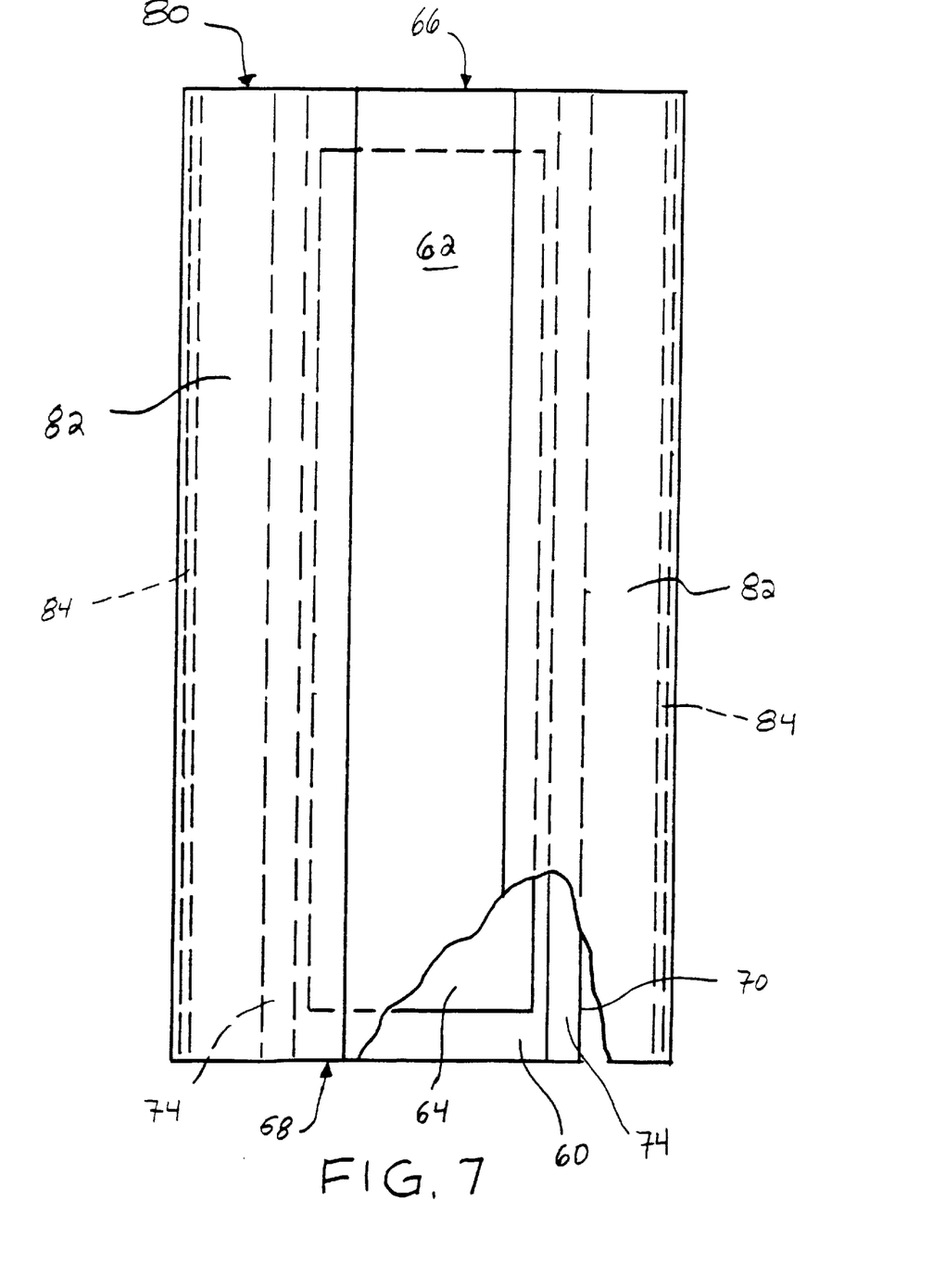
FIG. 7 is a top plan view showing an alternate absorbent assembly for use in an absorbent garment according to the present invention, with portions broken away for purposes of illustration.

Various alternate absorbent assemblies can be constructed and utilized with the present invention. One such alternate absorbent assembly 80 is illustrated in FIG. 7, where components similar to those previously described have been given the same reference numeral. The absorbent assembly 80 includes an absorbent core 64 sandwiched between a moisture barrier 60 and a bodyside liner 62. The absorbent assembly 80 also includes containment flaps 82 having several elastic strands 84 stretch bonded thereto. As illustrated, the containment flaps 82 are bonded to the bodyside liner 62 with the elasticized portion of each containment flap extending outward from a side edge 70. The containment flaps 82 could alternately be bonded to the moisture barrier 60 or between the bodyside liner 62 and the moisture barrier (not shown). The absorbent assembly 80 may optionally include cuff elastic bands 74 in addition to the containment flaps 82. The containment flaps 82 may be formed as disclosed in U.S. Pat. No. 4,704,116 issued Nov. 11, 1987, and U.S. Pat. No. 4,846,823 issued Jul. 11, 1989, to Enloe, which are incorporated herein by reference. The containment flaps 82 may also be attached in a foreshortened condition as disclosed in commonly assigned U.S. patent application Ser. No. 08/054,508 filed Apr. 26, 1993, by Popp et al. and titled "Foreshortened Containment Flaps in a Disposable Absorbent Article."

Figure 8:
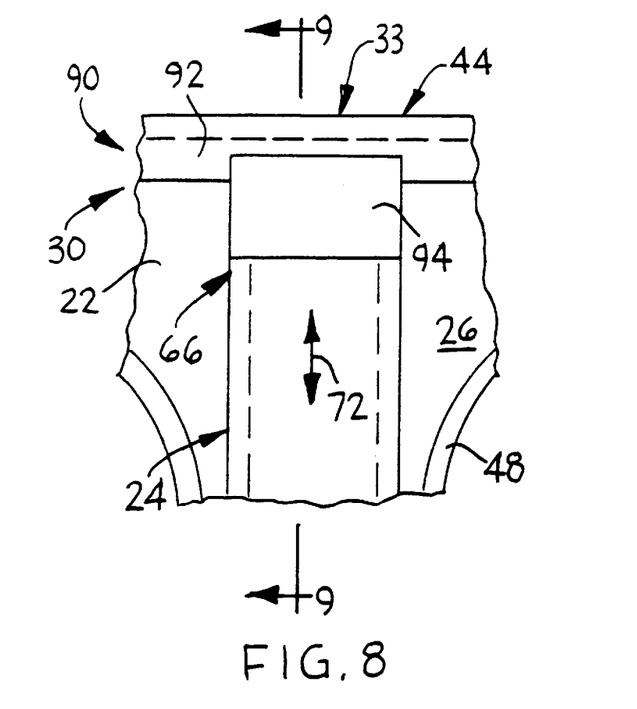
FIG. 8 is an enlarged view similar to FIG. 4, but illustrating an alternate connection of an absorbent assembly and an outer cover according to the present invention.
Figure 9:
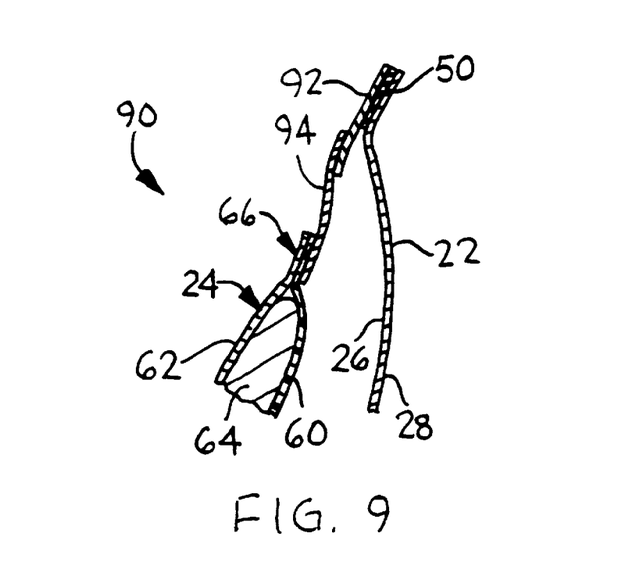
FIG. 9 is a view in section taken generally from the plane of the line 9—9 in FIG. 8.

A further alternate embodiment of the invention is illustrated in FIGS. 8 and 9 by a training pant 90, only particular portions of which are shown. In this embodiment, a tummy band 92 is formed of an elastic material that is capable of stretching in at least one direction. Although only the front waist region 30 is illustrated in FIGS. 8 and 9, it should be appreciated that the back waist region 32 can be constructed in a similar manner. The tummy band 92 is operatively joined to the outer cover 22 adjacent the waist opening 44. The tummy band 92 is stretchable in the direction parallel to the transverse axis of the training pant 90 to elasticize the waist opening 44.

A suspension member 94 is bonded to the outer cover 22, either indirectly as illustrated in FIGS. 8 and 9, or directly (not shown). The suspension member 94 is formed of an elastic material capable of stretching in at least one direction. The suspension member 94 is bonded to the outer cover 22 so that the suspension member material is stretchable in a direction parallel to the longitudinal axis of the training pant 90.

The suspension member 94 is also bonded to the absorbent assembly 24 so that the suspension member elastically connects an end 66 of the absorbent assembly and the outer cover 22. More precisely, the absorbent assembly 24 is bonded to one end of the suspension member 94, and an opposite end of the suspension member is directly bonded to the tummy band 92, which is in turn bonded to the outer cover 22. Alternately, the end of the suspension member 94 that is remote from the end attached to the absorbent assembly 24 may be directly bonded to the outer cover 22 (not shown). The resulting training pant 90 provides the same benefits described in relation to the training pant 20 illustrated in FIGS. 1–6, although two-way stretchable materials need not be used.

Figure 10:
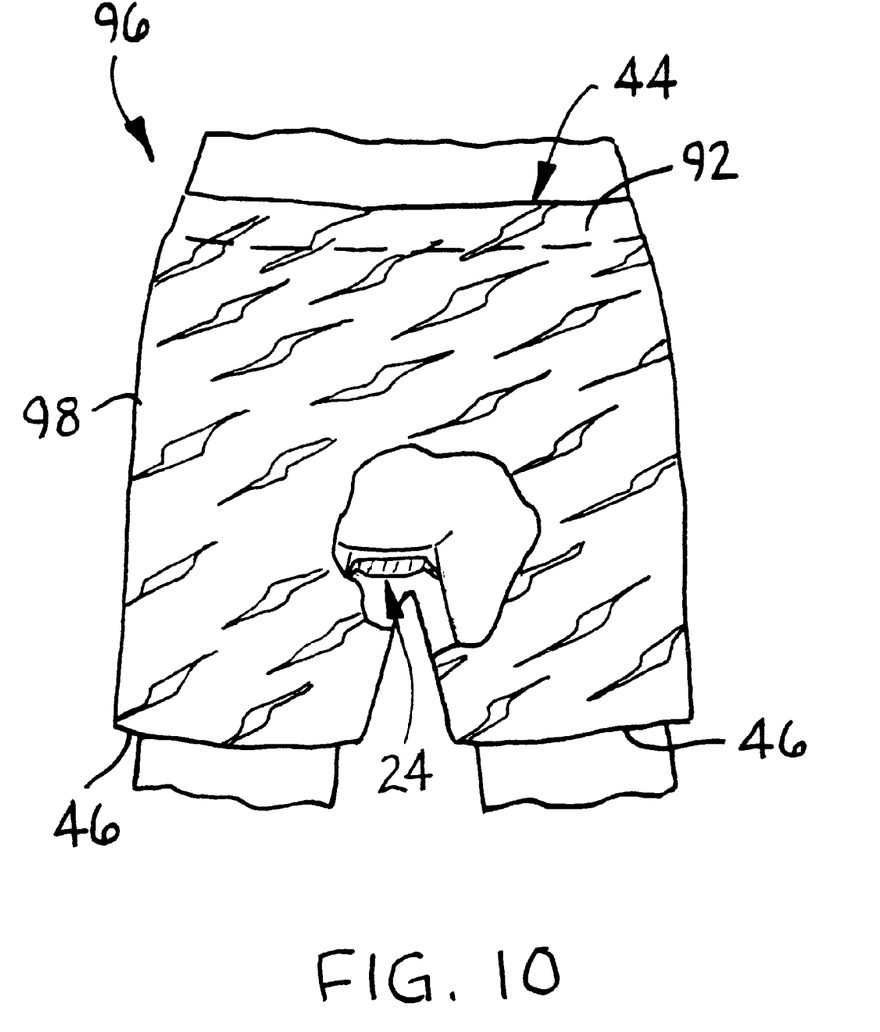
FIG. 10 is a perspective view of clothing apparel formed according to the present invention shown on a wearer, with portions broken away for the purposes of illustration.

A further alternate absorbent garment 96 according to the present invention is shown in FIG. 10. The garment 96 includes a three dimensional article of clothing apparel 98 and a suspended absorbent assembly 24. The illustrated clothing apparel 98, which functions as the outer cover, is in the form of a pair of shorts. The term clothing apparel, however, is intended generally to mean articles that are worn about the wearer's waist and that are not designed to be covered by other clothing. Thus, the term may encompass shorts, pants, skirts or the like. Such clothing apparel may but need not include elasticized leg openings.

The clothing apparel 98 defines a waist opening 44 and includes front and back waist regions 30 and 32. The illustrated clothing apparel 98 also includes a crotch area 34 located between the waist regions and a pair of leg openings 46. For embodiments in the form of a skirt (not shown), there may not be a crotch area or more than one leg opening.

The absorbent garment 96 also includes an elastic tummy band 92 and a suspension member 94 (not shown). The tummy band 92 is operatively joined to the clothing apparel 98 adjacent the waist opening 44 to elasticize the waist opening. The suspension member 94, also formed of an elastic material capable of stretching in at least one direction, is bonded to the clothing apparel 98 and to the absorbent assembly 24. The suspension member 94 elastically connects an end 66 of the absorbent assembly 24 and the clothing apparel 98, and is stretchable in a direction parallel to the longitudinal axis of the garment 96. The suspension member 94 may be bonded directly to the clothing apparel 98 or directly to the tummy band 92. Alternately, the garment 96 could include a tummy band formed of an elastic material capable of stretching in at least two directions, in which case the suspension member 94 need not be employed (not shown).

A wide variety of materials may be used to construct the aforementioned components of the training pant. Numerous examples of materials used in constructing training pants are described in the aforementioned U.S. patents and applications incorporated by reference herein. The outer cover 22, for example, may comprise a single layer of film, a woven material, a nonwoven material or another suitable liquid permeable or liquid impermeable material. The outer cover 22 may also comprise a laminate material, such as a two-layer composite including a liquid permeable nonwoven layer and a liquid impermeable film layer suitably joined together by adhesive. The leg and waist elastic bands 48 and 50 may be bonded to either element of the laminate or positioned between the layers and bonded to both. In another embodiment, the outer cover 22 may comprise a stretch bonded laminate formed of a prestretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Tex. under the trade name Kraton. Desirably, the outer cover 22 is both stretchable and impermeable to liquids.

Desirably, the outer cover material has an average actual drape value less than about 1.8 so that the outer cover follows body contours and is readily gatherable. The test procedure for determining the average actual drape value is ASTM Standard D-1388 entitled "Stiffness of Fabrics" and Method 5206 Federal Test Methods Standard #191A. Equipment used in the test procedure includes a Cantilever Bending Tester, Model 79-10 available from Testing Machines Inc., 400 Bayview Avenue, Amityville, N.Y., 11701; a 30 inch by 30 inch precision paper cutter with sample holder; and a cutting press with 1 inch by 6 inch rectangular cutting die. In performing this test, 5 outer cover material samples are cut into strips having a length of 6 inches and a width of 1 inch. Each strip is moved at a rate of 4¾ inches per minute in a direction parallel to its long dimension, so that its leading edge projects from the edge of a horizontal surface. The length of the overhang is measured when the tip of the strip depresses under its own weight to a point where the line joining the tip to the edge of the platform makes an angle of 41.5 degrees with the horizontal. Once a strip is depressed to the angle of 41.5 degrees, its length is measured, and the actual drape value is calculated by dividing the measured length in inches by 2. After performing this test on each of the 5 samples, the 5 actual drape values are averaged to determine the average actual drape value.

As described previously, the tummy bands 54 and 92 may be formed of a material capable of stretching in one direction or capable of stretching in at least two substantially perpendicular directions. One suitable one-directional stretch material is disclosed in U.S. Pat. No. 4,720,415 issued Jan. 19, 1988, to Vander Wielen et al., which is incorporated herein by reference. The one-directional stretch material may comprise a composite material including at least one gatherable web bonded to at least one elongated elastic web. The elastic web may be an elastic film or nonwoven fibrous elastic webs such as meltblown elastomeric fibrous webs. In one embodiment, the tummy bands comprise a stretch bonded laminate formed of a prestretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Tex. under the trade name Kraton. Other suitable one-directional stretch materials are disclosed in U.S. Pat. No. 4,606,964 issued Aug. 19, 1986, to Wideman and U.S. Pat. No. 4,657,802 issued Apr. 14, 1987, to Morman.

Suitable two-directional stretch materials for the tummy bands 54 and 92 are disclosed in U.S. Pat. No. 5,114,781 issued May 19, 1992, and U.S. Pat. No. 5,116,662 issued May 26, 1992, to Morman, which are incorporated herein by reference. A two-directional stretch material may comprise a composite material including a neckable material and an elastic sheet, which may be formed by meltblowing or extrusion. Neckable materials are those which may be constricted in at least one dimension by applying a tensioning force in a direction perpendicular to the desired direction of neck-down, and may include a spunbonded, meltblown or bonded carded web. The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

The moisture barrier 60 may comprise a thin, substantially liquid impermeable web or sheet of plastic film such as polyethylene, polypropylene, polyvinyl chloride or similar material. Alternately, the moisture barrier 60 may comprise a nonwoven, fibrous web which has been suitably constructed and arranged to be substantially liquid impermeable. Still alternately, the moisture barrier may comprise a layered or laminated material, such as a thermally bonded plastic film and nonwoven web composite.

The bodyside liner 62 may be any soft, flexible, porous sheet which passes fluids therethrough. The bodyside liner 62 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 62 has a pore size that readily allows the passage therethrough of liquids, such as urine and other body exudates. The liner 62 may be selectively embossed or perforated with discrete slits or holes extending therethrough. Optionally, the web or sheet may be treated with a surfactant to aid in liquid transfer. One suitable bodyside liner material is a wettable spunbonded polypropylene web produced by the methods and apparatus described in U.S. Pat. No. 4,340,563 issued Jul. 20, 1982, and U.S. Pat. No. 4,405,297 issued Sep. 23, 1983, to Appel et al., which are incorporated herein by reference.

In addition to those materials previously described, the absorbent core 64 may comprise an air-formed batt of cellulosic fibers (i.e., wood pulp fluff). Optionally, the absorbent core 64 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 64 may also include compounds to increase its absorbency, such as an effective amount of organic or inorganic high-absorbency materials. For example, the absorbent core 64 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst-Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 64 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the moisture barrier 60. Alternatively, the high-absorbency material can comprise a discrete layer separate from the fibrous material of the absorbent core 64, or can comprise a discrete layer integral with the absorbent core.

The absorbent core 64 may also include a tissue wrap layer to help maintain the integrity of the fibrous core. This tissue wrap typically comprises a hydrophilic cellulosic material, such as creped wadding or a high wet-strength tissue.

The leg and waist elastic bands 48 and 50 may be formed of a stretch bonded laminate. In particular, the stretch bonded laminate may comprise at least one nonwoven gatherable layer and an elastic layer. Alternately, the leg and waist elastic bands 48 and 50 may be formed of a dry-spun coalesced multifilament elastomeric thread sold under the tradename LYCRA and available from I.E. Du Pont de Nemours and Company. Still alternately, the elastic bands may be formed of other typical elastics utilized in the diaper-making art, such as a thin ribbon of elastic material as disclosed in U.S. Pat. No. 4,940,464 issued Jul. 10, 1990, to Van Gompel et al., which is incorporated herein by reference. Elasticity could also be imparted to the longitudinal side sections by extruding a hot melt elastomeric adhesive between the moisture barrier 60 and the bodyside liner 62. Other suitable elastic gathering means are disclosed in U.S. Pat. No. 4,938,754 to Mesek and U.S. Pat. No. 4,388,075 to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, only one rather than both ends of the absorbent assembly can be elastically connected to the outer cover. Also, the waist elastic bands 50 could be eliminated or formed as a portion of the tummy bands. Therefore, the invention should not be limited by the specific embodiments described, but only by the claims.

I claim:

1. An absorbent garment, comprising:

an outer cover defining opposite waist regions;

an absorbent assembly having a longitudinal axis and opposite longitudinally spaced ends, the absorbent assembly comprising an absorbent core and a moisture barrier; and a tummy band formed of an elastic material adapted to stretch in a first direction and a second direction substantially perpendicular to the first direction, the tummy band operatively joined to the outer cover adjacent at least a portion of one of the waist regions, the tummy band elastically connecting one end of the absorbent assembly and the outer cover, the first direction being generally parallel to the longitudinal axis of the absorbent assembly.

2. The absorbent garment of claim 1, wherein the absorbent assembly has a longitudinal length, each of the opposite longitudinally spaced ends of the absorbent assembly comprises from about 2 to about 9 percent of the longitudinal length, and a central portion between the opposite longitudinally spaced ends is not attached to the outer cover.

3. The absorbent garment of claim 1, wherein the absorbent core has a bulk thickness of not more than about 0.6 centimeter, an absorbent capacity of at least about 300 grams, and is comprised of substantially hydrophilic fibers and particulate high-absorbency material in a fiber-to-particulate ratio between about 30:70 and about 70:30.

4. A three-dimensional absorbent garment, comprising:

a full outer cover defining a waist opening and a pair of leg openings;

an absorbent assembly having a longitudinal axis and opposite longitudinally spaced ends, the absorbent assembly comprising an absorbent core and a moisture barrier; and a tummy band formed of an elastic material adapted to stretch in a first direction and a second direction substantially perpendicular to the first direction, the tummy band operatively joined to the outer cover adjacent at least a portion of the waist opening, the tummy band elastically connecting one end of the absorbent assembly and the outer cover, the first direction being generally parallel to the longitudinal axis of the absorbent assembly.

5. The absorbent garment of claim 4, wherein a pair of tummy bands are operatively joined to the outer cover, each tummy band elastically connecting one of the opposite longitudinally spaced ends of the absorbent assembly and the outer cover.

6. The absorbent garment of claim 5, wherein the tummy bands each have a width dimension between about 10 and about 50 percent of the total garment length.

7. The absorbent garment of claim 4, wherein the outer cover comprises an article of clothing apparel.

8. An absorbent garment, comprising:

an outer cover defining opposite waist regions;

an absorbent assembly having a longitudinal axis, opposite longitudinally spaced ends and side edges extending between the longitudinally spaced ends, the absorbent assembly comprising an absorbent core, a moisture barrier, and elastic members positioned along the side edges and bonded to the moisture barrier, the absorbent core having an absorbent capacity of at least about 500 grams; and at least one suspension member formed of an elastic material and elastically connecting at least one of the longitudinally spaced ends of the absorbent assembly and the outer cover, the suspension member being adapted to stretch in a direction generally parallel to the longitudinal axis of the absorbent assembly.

9. The absorbent garment of claim 8, further comprising a tummy band formed of an elastic material and operatively joined to the outer cover adjacent at least a portion of one of the waist regions.

10. The absorbent garment of claim 8, wherein the suspension member has first and second opposite ends, the first end bonded directly to the absorbent assembly and the second end bonded to the outer cover.

11. The absorbent garment of claim 8, wherein a pair of suspension members formed of an elastic material elastically connect the absorbent assembly and the outer cover.

12. The absorbent garment of claim 8, wherein the garment is three dimensional and the outer cover comprises an article of clothing apparel.

13. A three-dimensional absorbent garment, comprising:

a full outer cover including an inner surface and an opposite outer surface and defining a waist opening and a pair of leg openings;

a tummy band formed of an elastic material and operatively joined to the outer cover adjacent at least a portion of the waist opening;

an absorbent assembly having a longitudinal axis, opposite longitudinally spaced ends and side edges extending between the ends, the absorbent assembly comprising:

a liquid permeable liner;

a liquid impermeable moisture barrier attached to the liner; and an absorbent core sandwiched between the liner and moisture barrier, the absorbent core having a bulk thickness of not more than about 0.5 centimeter and an absorbent capacity of at least about 500 grams;

elasticized containment flaps attached to the absorbent assembly; and a pair of suspension members each formed of an elastic material and elastically connecting an end of the absorbent assembly and the inner surface of the outer cover, each suspension member being adapted to stretch in a direction generally parallel to the longitudinal axis of the absorbent assembly.

14. The absorbent garment of claim 13, wherein the absorbent core is comprised of substantially hydrophilic fibers and particulate high-absorbency material in a fiber-to-particulate ratio between about 40:60 and about 60:40.

15. The absorbent garment of claim 13, wherein the absorbent assembly is attached to the outer cover only at its spaced ends.

16. The absorbent garment of claim 13, further comprising leg elastic bands operatively joined to the outer cover about the leg openings.

17. The absorbent garment of claim 13, wherein the outer cover comprises a stretch bonded laminate formed of a prestretched elastic meltblown inner layer sandwiched between and attached to a pair of nonwoven webs, the laminate having an average actual drape value less than about 1.8.

18. The absorbent garment of claim 13, wherein the absorbent assembly further comprises elastic members positioned along the side edges and bonded to the moisture barrier.

19. The absorbent garment of claim 8, further comprising elasticized containment flaps attached to the absorbent assembly.

* * * * *